United States Patent [19]

Wilkinson et al.

[11] Patent Number: 4,819,675
[45] Date of Patent: Apr. 11, 1989

[54] CHEMICAL REMOVAL OF DENTAL PLAQUE

[75] Inventors: Edward L. Wilkinson, New Hope; David C. Sayles, Huntsville, both of Ala.

[73] Assignee: The United States of America as represented by the Secretary of the Army, Washington, D.C.

[21] Appl. No.: 192,740

[22] Filed: May 5, 1988

[51] Int. Cl.$^4$ .............................................. A61C 15/00
[52] U.S. Cl. ..................................................... 132/321
[58] Field of Search ............... 132/321, 322, 323, 324, 132/325, 326, 327, 328, 329; 433/216, 141

[56] References Cited

U.S. PATENT DOCUMENTS

| | | | |
|---|---|---|---|
| 2,667,443 | 1/1954 | Ashton | 132/321 |
| 3,771,536 | 11/1973 | Dragan | 132/321 |
| 4,414,990 | 11/1983 | Yost | 132/321 |

Primary Examiner—Gene Mancene
Assistant Examiner—Adriene J. Lepiane
Attorney, Agent, or Firm—Freddie M. Bush; James T. Deaton

[57] ABSTRACT

A method and a product employed in the method for the mechanical and chemical removal of dental plaques are disclosed. The method comprises providing cotton filaments of a size suitable for passing between teeth as a dental floss, chemically impregnating the cotton filaments by soaking in a saturated solution of potassium hydrogen tartrate and potassium hydrogen citrate, subsequently drying the chemically impregnated cotton fibers, and passing the dried chemically impregnated cotton filaments in the form of a dental floss between teeth and over the surfaces of the teeth containing plaque compositions including a calcium phosphate to thereby convert the calcium phosphate to the more soluble compounds calcium citrate and calcium tartrate which go into solution and the plaque is, thus, removed from the surfaces of the teeth. The method can alternately include the wetting agent polyoxyethylated sorbitan monooleate to enhance the penetration of the impregnated chemicals through mucin for reaction with calcium phosphate. The product prepared as described hereinabove can also be coated with paraffin wax after the drying step is completed and prior to using the product as a chemically impregnated dental floss.

5 Claims, No Drawings

CHEMICAL REMOVAL OF DENTAL PLAQUE

DEDICATORY CLAUSE

The invention described herein may be manufactured, used, and licensed by or for the Government for governmental purposes without the payment to us of any royalties thereon.

BACKGROUND OF THE INVENTION

Plaque is a localized abnormal patch on a body part or surface. Plaque which tightly binds to a tooth's surface in the form of a deposit is the subject matter to which the present invention relates. The source of this plaque is saliva which is a mixed secretion, produced mainly by three pairs of glands, the submaxillary, sublingual and parotid and to a lesser extent by the mucous membrane and the buccal glands of the mouth, throat and esophagus. It is a viscous, frothy, slightly opalescent fluid containing many substances. The salivary glands possess two kinds of cells: the serous or albuminous which secretes a fluid containing calcium phosphate, protein and enzyme; and the mucous cells which secrete a ropy fluid containing the glycoprotein mucin. A mixed secretion is obtained from the submaxillary gland which has both serous and mucous cells. The sublingual glands are chiefly mucous, and the parotid glands are chiefly serous.

On the basis of analysis by various investigators, the water content of human mixed saliva may be set at approximately 99.4 percent. The amount of total solids is 0.6 percent, about one-third is composed of inorganic constituents and the remainder of organic substances, including mucin, enzymes and epithelial cell debris.

The pH of saliva ($-\log [H+]$) varies from 5.75 to 7.05. The reaction of saliva, however, is usually slightly acidic, and the salivary pH falls just before and remains low just after meals. Between meals, the reaction of saliva approaches neutrality.

Plaque, if not removed daily, can result in a locus of bacteria which produce waste products which interact with the saliva and produce products which irritates the gums. The gums, under these circumstances, undergo swelling, bleed readily, and recede from the teeth. The result of plaque not being removed from the teeth can thus be an ultimate cause of periodontal disease.

Dental floss is presently used for the mechanical removal of food particles. An advantage is recognized for a dental floss which is impregnated with a chemical that facilitate the conversion of calcium phosphate to a more soluble calcium compound.

Therefore, an object of this invention is to provide an impregnated floss containing an acid salt and a wetting agent for use in chemical removal of dental plaque.

Another object of this invention is to provide a method of preparing impregnated cotton filaments to yield a dental floss for use in chemical removal of dental plaque.

SUMMARY OF THE INVENTION

Cotton filaments (of a size suitable for passing between teeth as floss) are impregnated by first soaking in a saturated solution of potassium hydrogen tartrate and potassium hydrogen citrate. The impregnated floss is then passed through a drying oven to remove the moisture. Coating the impregnated floss with paraffin wax is optional.

DESCRIPTION OF THE PREFERRED EMBODIMENT

A saturated solution of potassium hydrogen tartrate and potassium hydrogen citrate (a product which occur in wine lees) is a preferred solution for impregnating cotton filaments in the preparation of chemically impregnated dental floss.

The method of chemical removal of dental plaque employs chemically impregnated cotton filaments as a dental floss. This dental floss is prepared by the process which comprises providing cotton filaments of a suitable size for passing between teeth as a dental floss, impregnating the cotton filaments by soaking in a saturated solution potassium hydrogen tartrate and potassium hydrogen citrate which additionally contains a wetting agent of polyoxyethylated sorbitan monooleate, and drying the floss by passing it through drying oven to remove the moisture. Coating the impregnated floss with paraffin wax is optional which facilitates the use and stabilizing the floss until used.

The mechanism for this floss activity is as follows: The purpose of the wetting agent is to insure the penetration of the potassium hydrogen citrate or tartrate through the mucin to react with the calcium phosphate. When reaction occurs, the calcium citrate or tartrate being more soluble, goes into solution and is, thus removed from the surface of the teeth.

The benefit of the chemically impregnated dental floss of this invention over mechanical scraping by a dental technician is that build-up of tightly bound plaque is prevented during routine flossing. Routine flossing with the chemically-impregnated dental floss should remove the potential risk associated with plaque as the precursor for periodontal disease.

We claim:

1. A method for the mechanical and chemical removal of dental plaque employing chemically impregnated cotton filaments in the form of a dental floss, said method comprising:
   (i) providing cotton filaments of a size suitable for passing between teeth as a dental floss;
   (ii) impregnating said cotton filaments by soaking in a saturated solution of potassium hydrogen tartrate and potassium hydrogen citrate to form chemically impregnated cotton filaments;
   (iii) drying said chemically impregnated cotton filaments to remove moisture; and,
   (iv) passing said dried chemically impregnated cotton filaments in the form of a dental floss between teeth and over the surfaces of the teeth which are coated with plaque compositions containing a calcium phosphate compound to thereby contact said calcium phosphate compound of said plaque compositions with said potassium hydrogen tartrate and said potassium hydrogen citrate contained in said floss to cause a reaction to occur to convert said calcium phosphate to the more soluble compounds of calcium citrate and calcium tartrate which go into solution, and the plaque is, thus, removed from the surfaces of the teeth.

2. The method of claim 1 wherein said saturated solution of potassium hydrogen tartrate and potassium hydrogen citrate additionally contains a wetting agent of polyoxyethylated sorbitan monooleate to enhance the penetration of potassium hydrogen tartrate and potassium hydrogen citrate through mucin for reaction with said calcium phosphate.

3. The method of claim 2 wherein said dried impregnated cotton filaments are coated with paraffin wax prior to using as dental floss.

4. A chemically impregnated dental floss comprising:
(i) cotton filaments of a size suitable for passing between the teeth;
(ii) potassium hydrogen tartrate and potassium hydrogen citrate impregnated into said cotton filaments from a saturated solution containing said tartrate and said citrate; and
(iii) a paraffin wax coating on said chemically impregnated dental floss which is applied subsequent to drying said cotton filaments impregnated with said potassium hydrogen tartrate and said potassium hydrogen citrate.

5. The chemically impregnated dental floss of claim 4 additionally containing a wetting agent of polyoxyethylated sorbitan monooleate.

* * * * *